United States Patent [19]

Garst et al.

[11] Patent Number: 5,550,115
[45] Date of Patent: Aug. 27, 1996

[54] BIOLOGICALLY ACTIVE COMPOSITION

[75] Inventors: Roger H. Garst, Cincinati; Jane C. Mueninghoff, West Chester; Matthew C. Schwan, Cincinnati, all of Ohio

[73] Assignee: Henkel Corporation, Plymouth Meeting, Pa.

[21] Appl. No.: 452,059

[22] Filed: May 26, 1995

Related U.S. Application Data

[63] Continuation of Ser. No. 227,934, Apr. 15, 1994, abandoned.

[51] Int. Cl.$^6$ .............................. C07G 3/00; C07H 15/04; A01N 43/04; A61K 31/70
[52] U.S. Cl. ............................. 514/25; 514/53; 514/54; 536/4.1; 536/120
[58] Field of Search .................... 536/4.1, 116, 120; 514/25, 53, 54

[56] References Cited

U.S. PATENT DOCUMENTS

| | | | |
|---|---|---|---|
| H303 | 7/1987 | Malik et al. | 514/85 |
| 4,888,325 | 12/1989 | Schroeder et al. | 536/4.1 |
| 4,923,685 | 5/1990 | Wuelknitz et al. | 424/54 |
| 5,145,665 | 9/1992 | Klueppel et al. | 514/25 |
| 5,292,500 | 3/1994 | Wuelknitz et al. | 424/49 |

FOREIGN PATENT DOCUMENTS 5-43403  2/1993  Japan.

OTHER PUBLICATIONS

Partyka, et al., "The Adsorption Of Non-Ionic Surfactants On a Silica Gel", *Colloids and Surfaces*, 12, (1984) 255–270.

*Primary Examiner*—John Kight, III
*Assistant Examiner*—Everett White
*Attorney, Agent, or Firm*—Wayne C. Jaeschke; John E. Drach; Steven J. Trzaska

[57] ABSTRACT

A composition in dry form which can easily undergo dry blending and milling contains biologically active materials and a solid surfactant composed of a combination of an alkyl polyglycoside and an inert carrier selected from the group consisting of silica, talc, a zeolite, magnesium aluminum silicate, calcium sulfate, magnesium carbonate, magnesium oxide, aluminum oxide.

22 Claims, No Drawings

BIOLOGICALLY ACTIVE COMPOSITION

This application is a continuation of application Ser. No. 08/227,934 filed on Apr. 15, 1994 now abandoned.

BACKGROUND OF THE INVENTION

1. Field of the Invention

This invention relates to solid compositions containing biologically active materials and liquid surfactants and methods of treating agricultural substrates with such compositions.

2. Description of the Related Art

Insecticides, insect repellents, fungicides, bactericides, bacteriostats, herbicides, and plant growth regulators are normally formulated into various products for use on crops, for insect control, weed control and the like. In some cases, the products are formulated as a liquid or a semi-solid dispersion. Whether the method of application is dry or wet, dispersing agents are normally incorporated into such compositions to control the flow of the product to ensure equal distribution of the active ingredient through the remaining components of the composition.

It is known that alkyl polysaccharides can be used as dispersing agents and/or emulsifiers in compositions containing biologically active materials such as insecticides, insect repellents, fungicides, bactericides, bacteriostat, herbicides, plant growth regulators and the like. Alkyl polyglycosides are particularly effective in such applications because they are effective dispersants which are also environmentally safe.

The use of alkyl polyglycosides as dispersants and/or emulsifiers in dry compositions containing biologically active materials tend to make the formulations tacky and thus make subsequent milling and/or dry formulating operations difficult.

The compositions according to the present invention contain solid surfactants which are combinations of alkyl polyglycosides and inert carriers. Compositions containing biologically active materials and a combination of alkyl polyglycosides and inert carriers assume a dry form which can easily undergo dry blending and milling.

SUMMARY OF THE INVENTION

It is an object of the present invention to introduce a liquid surfactant into a solid phase agricultural chemical formulation without the resulting combination becoming tacky. It is a further object of the present invention to introduce a liquid nonionic surfactant into a solid phase agricultural chemical formulation which contains fungicides; bactericides, bacteriostat; insecticides; insect repellents; herbicides and/or plant growth regulators and mixtures thereof so that the liquid nonionic surfactant can function as an effective emulsifier when the agricultural chemical formulation is mixed with water.

It has been discovered that compositions containing biologically active materials and a solid phase surfactant assume a dry form which can easily undergo dry blending and milling. The solid phase surfactant is comprised of a combination of an alkyl polyglycoside and an inert carrier. The compositions according to the invention allow a liquid nonionic surfactant such as an alkyl polyglycoside to be incorporated into a solid composition containing a biologically active material which includes an insecticide, insect repellent, fungicide, bactericides, bacteriostat, herbicide, a plant growth regulator and the like. The alkyl polyglycoside surfactants assume a dry form while in combination with the inert carrier and are readily desorbed in aqueous media.

A further aspect of the invention is a method of treating an agricultural substrate comprising introducing to the substrate a sufficient amount of a composition which is comprised of a biologically active material which includes an insecticide, insect repellent, fungicide, a bactericide, bacteriostat, herbicide, a plant growth regulator and the like and a solid phase surfactant which is comprised of a combination of an alkyl polyglycoside and an inert carrier along with other adjuvants typically used in agricultural chemical formulations.

DETAILED DESCRIPTION OF THE INVENTION

Other than in the claims and in the operating examples, or where otherwise indicated, all numbers expressing quantities of ingredients or reaction conditions used herein are to be understood as modified in all instances by the term "about".

The term agricultural substrate as used herein means a plant, a plant pest, or a combination of a plant and a plant pest. A plant pest is defined as any living stage of any insects, mites, nematodes, slugs, snails, protozoa, or other invertebrate animals, bacteria, fungi, other parasitic plants or reproductive parts thereof, viruses, or any organisms similar to or allied with any of the foregoing, or any infectious substances which can directly or indirectly injure or cause disease or damage in any plants or parts thereof, or any processed, manufactured, or other products of plants.

The solid phase surfactant according to the invention is comprised of a combination of an inert carrier and an alkyl polyglycoside which is a compound of the formula I $$R_1O(Z)_a \qquad \qquad I$$

wherein $R_1$ is a monovalent organic radical having from about 6 to about 30 carbon atoms; Z is saccharide residue having 5 or 6 carbon atoms; a is a number having a value from 1 to about 6. The alkyl polyglucosides which can be used in the compositions and processes according to the invention are commercially available, for example, as APG® surfactants, Glucopon® surfactants, Agrimul® surfactants, or Plantaren® surfactants from Henkel Corporation, Ambler, Pa., 19002.

Examples of such surfactants include but are not limited to:
1. Agrimul® PG 2067 Surfactant - an alkylpolyglycoside in which the alkyl group contains 8 to 10 carbon atoms and having an average degree of polymerization of 1.7.
2. APG® 425 Surfactant - an alkyl polyglycoside in which the alkyl group contains 8 to 16 carbon atoms and having an average degree of polymerization of 1.6.
3. APG® 625 Surfactant - an alkyl polyglycoside in which the alkyl groups contains 12 to 16 carbon atoms and having an average degree of polymerization of 1.6.
4. APG® 300 Surfactant - an alkyl polyglycoside substantially the same as APG® 325 Surfactant but having an having an average degree of polymerization of 1.4.
5. Agrimul® PG 2069 Surfactant - an alkyl polyglycoside in which the alkyl groups contains 9 to 11 carbon atoms and having an average degree of polymerization of 1.6.
6. Glucopon® 600 Surfactant - an alkyl polyglycoside in which the alkyl groups contains 12 to 16 carbon atoms and having an average degree of polymerization of 1.4

7. Plantaren® 2000 Surfactant - a $C_{8-16}$ alkyl polyglycoside in which the alkyl group contains 8 to 16 carbon atoms and having an average degree of polymerization of 1.4.
8. Plantaren® 1300 Surfactant - a $C_{12-16}$ alkyl polyglycoside in which the alkyl groups contains 12 to 16 carbon atoms and having an average degree of polymerization of 1.6.

Other examples include alkyl polyglycoside surfactant compositions which are comprised of mixtures of compounds of formula I wherein Z represents a moiety derived from a reducing saccharide containing 5 or 6 carbon atoms; a is zero; and $R_1$ is an alkyl radical having from 8 to 20 carbon atoms. The composition is characterized in that it has increased surfactant properties and an HLB in the range of about 10 to about 16 and a non-Flory distribution of glycosides, which is comprised of a mixture of an alkyl monoglycoside and a mixture of alkyl polyglycosides having varying degrees of polymerization of 2 and higher in progressively decreasing amounts, in which the amount by weight of polyglycoside having a degree of polymerization of 2, or mixtures thereof with the polyglycoside having a degree of polymerization of 3, predominate in relation to the amount of monoglycoside, said composition having an average degree of polymerization of about 1.8 to about 3. Such compositions, also known as peaked alkyl polyglucosides, can be prepared by separation of the monoglycoside from the original reaction mixture of alkyl monoglycoside and alkyl polyglycosides after removal of the alcohol. This separation may be carried out by molecular distillation and normally results in the removal of about 70–95% by weight of the alkyl monoglycosides. After removal of the alkyl monoglycosides, the relative distribution of the various components, mono- and poly-glycosides, in the resulting product changes and the concentration in the product of the polyglycosides relative to the monoglycoside increases as well as the concentration of individual polyglycosides to the total, i.e. DP2 and DP3 fractions in relation to the sum of all DP fractions. Such compositions are disclosed in U.S. Pat. No. 5,266,690, the entire contents of which are incorporated herein by reference.

Preferred alkyl polyglycosides are those in which the alkyl groups contains from 8 to 12 carbon atoms and having an average degree of polymerization of 1.6 to 1.7. The most preferred alkyl polyglycosides are those which have alkyl groups containing 8 to 10 carbon atoms and having an average degree of polymerization of 1.7 and those which have alkyl groups containing 9 to 11 carbon atoms and having an average degree of polymerization of 1.6.

The inert carrier which can be used in the compositions and processes according to the invention is any solid substance which is insoluble in water and which will not interact unfavorably with or react with the other components of the compositions. For example, the inert carriers according to the invention can be silica, talc, a zeolite, magnesium aluminum silicate, calcium sulfate, magnesium carbonate, magnesium oxide, aluminum oxide. The preferred inert carrier is silica.

The relative amounts of alkyl polyglycoside and inert carrier which make up the solid phase surfactant can be expressed as a weight ratio of alkyl polyglycoside to inert carried and can range from 0.10 to 0.90. It is preferred that the solid phase surfactant have a weight ratio of alkyl polyglycoside to inert carrier of from 0.40 to 0.80 and most preferably from 0.60 to 0.65.

The solid phase surfactant can be made by any method known to those skilled in the art. One such method is disclosed in U.S. Pat. No. 5,364,647, the entire contents of which are incorporated herein by reference. In one preferred method of making the solid phase surfactants according to the invention, 5 to 65 parts by weight of alkyl polyglycoside of formula I are mixed with 35 to 95 parts by weight of silica and a quantity of water sufficient to produce a mixture which flows freely at a temperature below 80° C. The water is then removed from the mixture by any convenient means such as by spray drying, fluidized bed, or belt drying, so that the a free flowing powder is formed. In another preferred method of making the solid phase surfactants according to the invention, a hot, 50% aqueous solution of an alkyl polyglycoside is sprayed onto precipitated silica such that the resulting solid phase surfactant is comprised of 49% by weight of alkyl polyglycoside and 51% by weight of precipitated silica.

The solid phase surfactant thus formed can then be formulated with a biologically active material such as an insecticide, insect repellent, fungicide, bactericides, bacteriostat, herbicide, a plant growth regulator and the like along with other components typically used in such formulations and well known to those skilled in the art to form a formulation suitable for agricultural chemical applications. The solid phase surfactant according to the invention provides an emulsifier which readily enters the water phase when a composition containing the solid phase surfactant and a biologically active material is introduced into water for the purpose of applying it to a plant.

The amount of solid phase surfactant which can be formulated with a biologically active material according to the invention will depend upon the specific formulation and can be determined by those skilled in the art. Typically, the amount of solid phase surfactant will range from 1.0 to 10.0 percent by weight, preferably from 2.0 to 8.0 percent by weight, and most preferably from 3.0 to 5.0 percent by weight.

The biologically active materials which can be used to make compositions according to the invention include, but are not limited to insecticides such as O,O-diethyl O-(2-isopropyl-4-methyl-6-pyrimidinyl)phosphorothioate, O,O-diethyl S-2-[(ethylthio)ethyl]phosphorodithioate, O,O-dimethyl O-(3-methyl-4-nitrophenyl)thiophosphate, O,O-dimethyl-(N-methylcarbamoylmethyl)phosphorodithioate, O,O-dimethylS-(N-methyl-N-formylcarbamoylmethyl)phosphoro dithioate, O,O-dimethyl S-2-[(ethylthio)ethyl] phosphorodithioate, O,O-diethyl S-2-[(ethylthio)ethyl] phosphorodithioate, O,O-dimethyl-1-hydroxy-2,2,2-trichloroethylphosphonate, O,O-diethyl-O-(5-phenyl-3-isooxazolyl)phosphorothioate, O,O-dimethyl O-(2,5-dichloro-4-bromophenyl)phosphorothioate, O,O-dimethyl-O-)3-methyl-4-methylmercaptophenyl)thiophosphate, O-ethyl O-p-cyanophenyl-O-phenylphosphorothioate, O,O-dimethyl-S-(1,2-dicarboethoxyethyl)phosphorodithioate, 2-chloro-(2,4,5-trichlorophenyl)vinyldimethyl phosphate, 2-chloro-1-(2,4-dichlorophenyl)vinyldimethyl phosphate, O,O-dimethyl O-p-cyanophenyl phosphorothioate, 2,2-dichlorovinyl dimethyl phosphate, O,O-diethyl O-2,4-dichlorophenyl phosphorothioate, ethyl mercaptophenylacetate O,O-dimethyl phosphorodithioate, S-[(6-chloro-2-oxo-3-benzooxazolinyl)methyl]O,O-diethyl phosphorodithioate, 2-chloro-1-(2,4-dichlorophenyl)vinyl diethylphosphate O,O-diethyl O-(3-oxo-2-phenyl-2H-pyridazine-6-yl)phosphorothioate, O,O-dimethyl S-(1-methyl-2-ethylsulfinyl)-ethyl phosphorothiolate, O,O-dimethyl S-phthalimidomethyl phosphorodithioate, O,O-diethyl 2,2,2-trichloroethanol, 2-(p-tert-butyl-phenoxy)isopropyl-2'-chloroethylsulfite, azoxybenzene, di-(p-chlorophenyl)-cyclopropyl carbinol, di[tri(2,2-dimethyl-2-phenylethyl)tin] oxide, 1-(4-chlorophenyl)-3-(2,6-difluorobenzoyl)urea and S-tricyclohexyltin O,O-diisopropylphosphorodithioate; 2-methyl-2-(methylthio)propionaldehyde O-(mehtylcarbamoyl)oxime; ethyl [2-(4-phenoxyphenoxy)ethyl]carbamate; butyl-2,3-dihydro-2,2-dimethylbenzofuran-7-yl N,N'-dimethyl-N,N'-thiodicarbamate; 1-naphthyl methyl carbamate; 2-(ethylthiomethyl)phenyl methylcarbamate; 5-(4phenoxybutyl)dimethylthiocarbamate; dimethyl N,N'-(thiobis(methylimino)carbonyloxy)bis(ethanimidothioate); (RS)-α-cyano-3-phenoxybenzyl-(RS)-2-(4-chlorophenyl)-3-methylbutyrate; (RS)-α-cyano-3-phenoxyphenyl-(RS)-2,2-dichloro-1-(4-ethoxyphenyl)cyclopropanecarboxylate; (RS)-α-cyano-3-phenoxybenzyl-N-(2-chloro-α,α,α-trifluoro-p-tolyl-D-valinate; 3-phenoxybenzyl-(1RS)-cis,trans-3-(2,2-dichlorovinyl)-2,2-diemthylcyclopropanedicarboxylate.

Insect repellents which may also be employed include but are not limited to 2-ethyl-1,3 -hexanediol; N-octyl bicycloheptene dicarboximide; N,N-diethyl-M-toluamide; 2,3:4,5-Bis (2-butylene) tetrahydro-2-furaldehyde; Di-n-propyl isocinchomeronate; and 2-hydroxyethyl-n-octyl sulfide.

Fungicides which may also be employed include but are not limited to 3,3'-ethylenebis (tetrahydro-4,6-dimethyl-2H-1,3,5-thiadiazine-2-thione), zinc or manganese ethylenebis-(dithiocarbamate), bis-(dimethyldithiocarbamoyl)disulfide, zinc propylenebis (dithiocarbamate), bis(dimethyldithiocarbamoyl) ethylenediamine; nickel dimethyldithiocarbamate, methyl-1(butylcarbamoyl)-2-benzimidazolecarbamate, 1,2-bis(3-methoxycarbonyl-2-thioureido)benzene, 1-isopropylcarbamoyl-3-(3,5-dichlorophenyl)hydantoin, potassium N-hydroxymethyl-N-methyldithiocarbamate and 5-methyl-10-butoxycarbonylamino-10, 11-dehydrodibenzo (b,f)azepine; pyridine fungicides such as zinc bis(1-hydroxy-2(1H)pyridinethionate and 2-pyridinethiol-1-oxide sodium salt; O,O-diisopropyl S-benzylphosphorothioate and O-ethyl S,S-diphenyldithiophosphate; phthalimide fungicides such as N-(2,6-p-diethylphenyl)phthalimide and N-(2,6-diethylphenyl)-4-methylphthalimide; dicarboxyimide fungicides such as N-trichloromethylthio 4-cyclohexene-1,2-dicarboxyimide and N-tetrachloroethylthio-4-cyclohexene-1,2-dicarboxyimide; 5,6-dihydro-2-methyl-1,4-oxathine-3-carboxanilido-4,4-dioxide and 5,6-dihydro-2-methyl-1,4-oxathine-3-carboxanilide; naphthoquinone fungicides such as 2,3-dichloro-1,4-naphthoquinone, 2-oxy-3-chloro-1,4-naphthoquinone copper sulfate, pentachloronitrobenzene; 1,4-dichloro-2,5-dimethoxybenzene; 5-methyl-s-triazol-(3,4-b)benzthiazole; 2-(thiocyanomethylthio)benzothiazole; 3-hydroxy-5-methylisooxazole; N-2,3-dichlorophenyltetrachlorophthalamic acid; 5-ethoxy-3-trichloromethyl-1,2,4-thiaziazole; 2,4-dichloro-6-(0-chloroanilino)-1,3,5-triazine; 2,3-dicyano-1,4-dithioanthraquinone; copper 8-quinolinate; polyoxine; validamycin; cycloheximide; iron methanearsonate; diisopropyl 1,3-dithiolane-2-iridene malonate; 3-allyloxy-1,2-benzoisothiazol-1,1-dioxide; kasugamycin; Blasticidin S; 4,5,6,7-tetrachlorophthalide; 3-(3,5-dichlorophenyl)5-ethenyl5-methyloxazolizine-2,4-dione N-(3,5-dichlorophenyl)-1,2-dimethylcyclopropane-1,2-dicarboxyimide; S-n-butyl-5'-para-t-butylbenzyl-N-3-pyridyldithiocarbonylimidate; 4-chlorophenoxy-3,3-dimethyl-1-(1H,1,3,4-triazol-1-yl)-2-butanone; methyl-D,L-N-(2,6-dimethylphenyl)-N-(2'-methoxyacetyl)alaninate; N-propyl-N-[2-(2,4,6-trichlorophenoxy)ethyl]imidazol-1-carboxamide; N-(3,5-dichlorophenyl)succinamide; tetrachloroisophthalonitrile; 2-dimethylamino-4-methyl-5-n-butyl-6-hydroxypyrimidine; 2,6-dichloro-4-nitroaniline; 3-methyl-4-chlorobenzthiazol-2-one; 1,2,5,6-tetrahydro-4H-pyrrolol-[3,2,1-i,j]quinoline-2-one; 3'-isopropoxy-2-methylbenzanilide; 1-[2-(2,4-dichlorophenyl)-4-ethyl-1,3-dioxorane-2-ylmethyl]-1H,1,2,4-triazol; 1,2-benzisothiazoline-3-one; basic copper chloride; basic copper sulfate; N'-dichlorofluoromethylthio-N,N-dimethyl-N-phenyl sulfamide; ethyl-N-(3-dimethylaminopropyl)thiocarbamate hydrochloride; piomycin; S,S-6-methylquinoxaline-2,3-di-yldithiocarbonate; complex of zinc and manneb; di-zinc bis(dimethyldithiocarbamate) ethylenebis (dithiocarbamate).

Plant growth regulators which may also be employed include but are not limited to N-methoxycaronyl-N'-4-methylphenylcarbamoylethylisourea and 1-(4-chlorophenylcarbamoyl)-3-ethoxycarbonyl-2-methylisourea; another type of plant growth regulators such as sodium naphthaleneacetate, 1,2-dihydropyridazine-3,6-dione and gibberellins; traizine herbicides such as 2-methylthio-4,6-bisethylamino-1,3,5-triazine, 2-chloro-4,6-bisethylamino-1,3,5-triazine, 2-methoxy-4-ethylamino-6-isopropylamino-1,3,5-triazine, 2-chloro-4-ethylamino-6-isopropylamino-s-triazine, 2-methylthio-4,6-bis(isopropylamino)-S-triazine and 2-methylthio-4-ethylamino-6-isopropylamino-s-triazine; phenoxy herbicides such as 2,4-dichlorophenoxyacetic acid and methyl, ethyl, and butyl esters thereof. 2-chloro-4-methylphenoxyacetic acid, 4-chloro-2-methylphenoxyacetic acid and ethyl 2-methyl-4-chlorophenoxybutylate; diphenylether herbicides such as 2,4,6-trichlorophenyl-4'-nitrophenylether, 2,4-dichlorophenyl-4'-nitrophenylether and 3,5-dimethylphenyl-4'-nitrophenylether; urea herbicides such as 3-(3,4-dichlorophenyl)-1-methoxy-1-methyl urea, 3-(3,4-dichlorophenyl)-1,1-dimethylurea and 3-(4-chlorophenyl)-1,1-dimethyl urea; carbamate herbicides such as 3-methoxycarbonylaminophenyl-N-(3-methylphenyl)carbamate, isopropyl-N-(3-chlorophenyl)carbamate and methyl-N-(3,4'-dichlorophenyl)carbamate; uracil herbicides such as 5-bromo-3-sec-butyl-6-methyluracil and 1-cyclohexyl-3,5-propyleneuracil; thiolcarbamate herbicides such as S-(4-chlorobenzyl)-N,N-diethylthiolcarbamate, S-ethyl-N-cyclohexyl-N-ethylthiolcarbamate and S-ethyl-hexahydro-1H-azepine-1-carbothioate and S-ethyl-N,N-di-n-propyl-thiocarbamate; pyridinium herbicides such as 1,1'-dimethyl-4,4'-bispyridinium dichloride; phosphoric herbicides such as N-(phosphonomethyl)glycine; aniline herbicides such as alpha,alpha,alpha-trifluoro-2,6-dinitro-N,N-dipropyl-p-toluidine, 4-(methylsulfonyl)-2,6-dinitro-N,N-dipropylaniline and N[3],N[3]-diethyl-2,4-dinitro-6trifluoromethyl-1,3-phenylene diamine; acid anilide herbicides such as 2-chloro-2',6'-diethyl-N-(butoxymethyl)acetoanilide, 2-chloro-2',6'-diethyl-N-(methoxymethyl)acetoanilide, and 3,4-dichloropropioneanilide; pyrazole herbicides such as 1,3-dimethyl-4-(2,4-dichlorobenzoyl)-5-hydroxypyrazole and 1,3-di-methyl-4-(2,4-dichlorobenzoyl)-5-(p-toluenesulfonyloxy)pyrazole; 5-tert-butyl-3-(2,4-dichloro-5-isopropoxyphenyl)-1,3,4-oxadiazoline-2-one; 2-[N-isopropyl,N-(4-chlorophenyl)carbamoyl]-4-chloro-5-methyl-4-isooxazoline-3-one; 3-isopropylbenzo-2-thia-1,3-diazinone-(4)-2,4-dioxide and 3-(2-methyl-phenoxy)pyridazine. The compositions according to the invention may also contain, for example, dyes, additional surfactants and solvents where required. The following examples are meant to illustrate but not to limit the invention.

EXAMPLE 1

Surface Tension of Aqueous Dispersion of Solid Phase Surfactant

A solid phase surfactant prepared by spraying hot APG® 225 surfactant (a trademark product of Henkel Corporation, Ambler, Pa., 19002) onto Sippernat® 50 precipitated silica (a trademark product of DeGussa Corp.) such that the resulting solid phase surfactant is comprised of 49% by weight of the alkyl polyglycoside and 51% by weight of precipitated silica. The resulting solid phase surfactant was a uniform solid which was very dusty and exhibited only slight bridging and caking tendency. The surface tension of a 0.1% by weight aqueous solution of the solid phase surfactant was found to be 27.10 dynes/cm @25° C. The surface tension of a 0.1% by weight aqueous solution of APG® 225 surfactant was found to be 26.66 dynes/cm @ 25° C. The results show that the APG® 225 surfactant is substantially completely released from the solid phase surfactant when the solid phase surfactant is placed in water.

EXAMPLE 2

Wettable Powder Composition

A mixture of the following components should result in a wettable powder formulation according to the invention. A wettable powder composition containing Chlorothalonil can be prepared having the following composition:

| Component | Wt. % |
| --- | --- |
| Chlorothalonil (95%) | 78.94 |
| Agrimul PG ® 2069/Silica* | 3.00 |
| Lomar ® PW | 2.00 |
| Foamaster Soap L | 0.50 |
| Barden Clay | 15.56 |

EXAMPLE 3

Water Dispersible Granule Formulation

A mixture of the following components should result in a water dispersible granule composition according to the invention. A water dispersible granule composition containing Atrazine can be prepared having the following composition:

| Component | Wt. % |
| --- | --- |
| Atrazine (98%) | 91.83 |
| Agrimul PG ® 2069/Silica* | 2.75 |
| Lomar ® PW | 5.00 |
| Foamaster Soap L | 0.25 |
| HiSil 233 | 0.17 |

EXAMPLE 4

Water Dispersible Granule Formulation

A mixture of the following components should result in a water dispersible granule composition according to the invention. A water dispersible granule composition containing Fluometuron can be prepared having the following composition:

| Component | Wt. % |
| --- | --- |
| Tech. Fluometuron (97%) | 88.70 |
| Agrimul PG ® 2069/Silica* | 2.00 |
| Lomar ® PW | 3.00 |
| Foamaster Soap L | 0.50 |
| HiSil 233 | 5.80 |

* — weight ratio Agrimul PG ® 2069/Silica = 0.66 in all cases.

What is claimed is:

1. A composition comprising: (1) a biologically active ingredient selected from the group consisting of a fungicide; a bactericide, a bacteriostat; an insecticide; an insect repellent; an herbicide; a plant growth regulator and mixtures thereof and, (2) a solid phase surfactant comprised of (i) a compound of the formula I $$R_1O(Z)_a \qquad \text{I}$$

wherein $R_1$ is a monovalent organic radical having from about 6 to about 30 carbon atoms; Z is a saccharide residue having 5 or 6 carbon atoms; a is a number having a value from 1 to about 6, and (ii) an inert solid carrier selected from the group consisting of silica, talc, a zeolite, magnesium aluminum silicate, calcium sulfate, magnesium carbonate, magnesium oxide, aluminum oxide.

2. The composition of claim 1 wherein said inert solid carrier is silica.

3. The composition of claim 1 wherein the weight ratio of said compound of formula I to said inert solid carrier is from about 0.10 to about 0.90.

4. The composition of claim 3 wherein said weight ratio is from about 0.40 to about 0.80.

5. The composition of claim 4 wherein said weight ratio is from about 0.60 to about 0.65.

6. The composition of claim 1 wherein in said compound of the formula I $R_1$ is an alkyl group having from 8 to 10 carbon atoms and a is about 1.7.

7. The composition of claim 1 wherein in said compound of the formula I $R_1$ is an alkyl group having from 9 to 11 carbon atoms and a is about 1.6.

8. The composition of claim 1 wherein said biologically active ingredient is an herbicide.

9. The composition of claim 1 wherein said composition is comprised of from about 1.0 to about 10.0% by weight, based on the weight of said composition, of said solid phase surfactant, 10. The composition of claim 9 wherein said composition is comprised of from about 2.0 to about 8.0% by weight, based on the weight of said composition, of said solid phase surfactant.

11. The composition of claim 10 wherein said composition is comprised of from about 3.0 to about 5.0% by weight, based on the weight of said composition, of said solid phase surfactant.

12. A process for treating an agricultural substrate which comprises applying to said substrate an effective amount of a composition comprised of: (1) a biologically active ingredient selected from the group consisting of a fungicide; a bactericide; a bacteriostat; an insecticide; an insect repellent; an herbicide; a plant growth regulator and mixtures thereof and, (2) a solid surfactant comprised of (i) an alkyl polyglycoside of the formula I $$R_1O(Z)_a \qquad \text{I}$$

wherein $R_1$ is a monovalent organic radical having from about 6 to about 30 carbon atoms; Z is a saccharide residue having 5 or 6 carbon atoms; a is a number having a value from 1 to about 6, and (ii) an inert solid carrier selected from the group consisting of silica, talc, a zeolite, magnesium aluminum silicate, calcium sulfate, magnesium carbonate, magnesium oxide, aluminum oxide.

13. The process of claim 12 wherein said inert solid carrier is silica.

14. The process of claim 12 wherein the weight ratio of said compound of formula I to said inert solid carrier is from about 0.10 to about 0.90.

15. The process of claim 14 wherein said weight ratio is from about 0.40 to about 0.80.

16. The process of claim 15 wherein said weight ratio is from about 0.60 to about 0.65.

17. The process of claim 12 wherein in said compound of the formula I $R_1$ is an alkyl group having from 8 to 10 carbon atoms and a is about 1.7.

18. The process of claim 12 wherein in said compound of the formula I $R_1$ is an alkyl group having from 9 to 11 carbon atoms and a is about 1.6.

19. The process of claim 12 wherein said biologically active ingredient is an herbicide.

20. The process of claim 12 wherein said composition is comprised of from about 1.0 to about 10.0% by weight, based on the weight of said composition, of said solid phase surfactant.

21. The process of claim 20 wherein said composition, is comprised of from about 2.0 to about 8.0% by weight, based on the weight of said composition, of said solid phase surfactant.

22. The process of claim 21 wherein said composition is comprised of from about 3.0 to about 5.0% by weight, based on the weight of said composition, of said solid phase surfactant.

* * * * *